United States Patent
Feugnet et al.

(10) Patent No.: US 9,249,364 B2
(45) Date of Patent: Feb. 2, 2016

(54) PROCESS FOR CONVERTING A HEAVY FEED USING A CATALYTIC CRACKING UNIT AND A STEP FOR SELECTIVE HYDROGENATION OF THE GASOLINE OBTAINED FROM CATALYTIC CRACKING

(71) Applicant: IFP ENERGIES NOUVELLES, Rueil-Malmaison (FR)

(72) Inventors: Frédéric Feugnet, Lyons (FR); Francois Hugues, Vernaison (FR); Natacha Touchais, Vienne (FR); Hugues Dulot, Lyons (FR); Annick Pucci, Croissy sur Seine (FR)

(73) Assignee: IFP ENERGIES NOUVELLES, Rueil-Malmaison (FR)

( * ) Notice: Subject to any disclaimer, the term of this patent is extended or adjusted under 35 U.S.C. 154(b) by 211 days.

(21) Appl. No.: 13/767,072

(22) Filed: Feb. 14, 2013

(65) Prior Publication Data
US 2013/0211161 A1 Aug. 15, 2013

(30) Foreign Application Priority Data
Feb. 15, 2012 (FR) .................................... 12 00424

(51) Int. Cl.
| | |
|---|---|
| *C10G 69/12* | (2006.01) |
| *C07C 1/00* | (2006.01) |
| *C07C 2/12* | (2006.01) |
| *C10G 11/04* | (2006.01) |
| *C10G 11/05* | (2006.01) |

(52) U.S. Cl.
CPC ................ *C10G 69/126* (2013.01); *C07C 1/00* (2013.01); *C07C 2/12* (2013.01); *C10G 11/04* (2013.01); *C10G 11/05* (2013.01)

(58) Field of Classification Search
CPC ...... C10G 69/126; C10G 11/04; C10G 11/05; C07C 2/12; C07C 1/00
USPC ............................................ 208/71; 585/251
See application file for complete search history.

(56) References Cited

U.S. PATENT DOCUMENTS

| | | | | | |
|---|---|---|---|---|---|
| 4,973,790 | A | * | 11/1990 | Beech et al. ................... | 585/533 |
| 5,177,282 | A | | 1/1993 | Nierlich et al. | |
| 5,202,015 | A | | 4/1993 | Harandi | |
| 6,143,942 | A | | 11/2000 | Verrelst et al. | |
| 2012/0103867 | A1 | * | 5/2012 | Coupard et al. ................. | 208/57 |
| 2013/0281749 | A1 | * | 10/2013 | Feugnet et al. ............... | 585/315 |

OTHER PUBLICATIONS

Search Report of FR 1200424 (Sep. 5, 2012).
R. Van Grieken et al., "Nitrogen and Sulphur Poisoning in Alkene Oligomerization Over Mesostructured Aluminosilicates (Al-MTS, Al-MCM-41) and Nanocrystalline n-HZM-5", Applied Catalysis A: General, vol. 337 (2008) pp. 173-183.
E. Krivan et al., "Investigation of the Oligomerization of Light Olefins on Ion Exchange Resin Catalyst", Hungarian Journal of Industrial Chemistry, vol. 38, No. 1 (2010) pp. 53-57.

* cited by examiner

*Primary Examiner* — Randy Boyer
*Assistant Examiner* — Juan Valencia
(74) *Attorney, Agent, or Firm* — Millen, White, Zelano and Branigan, P.C.

(57) ABSTRACT

The present invention describes a process for converting a heavy feed which is flexible for the production of propylene, gasoline and middle distillate.
The process uses a catalytic cracking unit and a unit for the oligomerization of C4 to C9 olefins. The process of the invention includes selective hydrogenation of the unrefined gasoline cut obtained from the catalytic cracking unit and separation between a light gasoline cut and a heavy gasoline cut, the light gasoline being directed to the oligomerization unit.

15 Claims, 1 Drawing Sheet

PROCESS FOR CONVERTING A HEAVY FEED USING A CATALYTIC CRACKING UNIT AND A STEP FOR SELECTIVE HYDROGENATION OF THE GASOLINE OBTAINED FROM CATALYTIC CRACKING

FIELD OF THE INVENTION

The invention relates to a process for converting a heavy hydrocarbon feed exhibiting great flexibility for the production of middle distillate, gasoline and propylene.

The process of the present invention uses a catalytic cracking unit (FCC).

Generally, such catalytic cracking units are optimized with a view to the production of light products: liquefied gas (or LPG), light olefins and gasoline, in order to satisfy the needs of either the market for polymers obtained from the polymerization of light olefins or gasoline consumption requirements in the automotive industry.

Currently, given the substantial increase in the use of diesel in the automotive industry, the demand for products of the middle distillate type has increased substantially.

As a consequence, another mode of operation of the catalytic cracking unit has been developed, with a view to orientating production towards middle distillates.

The flexibility in and improvement to yields as regards one or other of the three products are accomplished by adding an oligomerization unit treating C4 to C9 olefins obtained from FCC or from other additional sources such as the coking unit, visbreaking unit, the unit for converting methanol into olefins or any other process for converting alcohols into olefins, steam cracking or indeed the Fischer-Tropsch synthesis unit, or from the paraffin dehydrogenation unit, used alone or as a mixture.

A description of coking, visbreaking and steam cracking units can be found in the reference work "Raffinage et génie chimique" [Refining and chemical engineering] by P Wuithier, published by Technip.

The oligomerization unit requires a purification step in order to reduce the quantity of nitrogen-containing compounds, which are poisonous to the reaction. The dienes and sulphur-containing compounds present in the oligomerization feed, which are inhibitors or poisonous to the reaction, are generally not reduced in that purification step and have a negative impact on the cycle period of the catalyst.

The present invention essentially consists of adding a step for selective hydrogenation of the gasoline leaving the FCC (i.e. upstream of the oligomerization unit), which can be used to limit the quantity of those inhibitors and thus increase the cycle period of the oligomerization catalyst without altering the distribution of the desired products.

EXAMINATION OF THE PRIOR ART

Patent application FR 2 935 377 concerns a process for converting a hydrocarbon feed termed a heavy feed with a view to the co-production of propylene and of gasoline with a minimum yield. The process of that invention comprises at least two reaction steps, a first, catalytic cracking step and a second step for the oligomerization of C3 and C4 olefins or C4 olefins or C4 and C5 olefins from the catalytic cracking step.

The process of the cited patent can be used to carry out two types of production, corresponding to two distinct working modes:
 a "maxi propylene" mode, corresponding to maximum production of propylene while keeping the gasoline yield to a minimum, or even slightly increased compared to the potential yield from the catalytic cracking unit alone; or
 a "maxi gasoline" mode, corresponding to maximum production of gasoline without the production of propylene.

In that patent, only C3, C4 and C5 olefins are mentioned.

Application FR 10/04585 describes a process for converting a heavy feed that can be used to improve the selectivity for middle distillate. The process uses a catalytic cracking unit followed by one or more units for the oligomerization of olefins containing 2 to 9 carbon atoms in order, preferably, to produce an additional middle distillate cut. The light portion of the oligomerizate produced, which cannot be incorporated into the middle distillate cut, is recycled to the FCC for cracking into light olefins which return to the oligomerization units as a supplement to the olefins of the feed in order, preferably, to form heavy oligomerizates which can be incorporated into the middle distillate cut.

In that application, the oligomerized C2 to C9 cut is constituted by a portion of the FCC products without carrying out any other processes before oligomerization.

Patent FR 2 797 639 B1 describes a process for the production of gasoline with a low sulphur content, comprising a step for selective hydrogenation of diolefins and optionally at least one step aimed at increasing the molecular weight of the light sulphur-containing products present in the gasoline. The cited patent describes separating the gasoline into two fractions: light gasoline and heavy gasoline, and can be used to produce low sulphur gasolines.

Patent FR 2 895 416 B1 describes a catalytic system that can be used to carry out joint selective hydrogenation of polyunsaturated compounds into monounsaturated compounds contained in the gasolines, as well as to make light sulphur-containing compounds heavier by reaction with the unsaturated compounds.

In the cited patents, the intended aim is to obtain a gasoline without substantial loss of octane number and with a low sulphur content, with the gasoline entering the fuel pool.

In the context of the present invention, using a selective hydrogenation unit on the gasoline cut obtained from the catalytic cracking unit before separating the light gasoline and the heavy gasoline means that a light C5-C9 gasoline cut can be obtained with a reduced quantity of diolefins and also of sulphur, which can be sent directly to the final purification unit (reduction of nitrogen-containing compounds) preceding the oligomerization unit. By using it this way, the cycle period for the oligomerization catalysts is significantly improved without altering the distribution of the desired products.

BRIEF DESCRIPTION OF THE FIGURES

FIG. 1 represents a layout of the process of the invention. The dashed lines represent the optional supplies or recycles. The notations assigned to the units are introduced in the remainder of the text.

BRIEF DESCRIPTION OF THE INVENTION

The invention consists in a process for converting a heavy hydrocarbon feed with great flexibility for the production of middle distillate, gasoline and propylene, using a catalytic cracking unit (FCC) followed by a unit for the selective hydrogenation (SHU) of the gasoline obtained from the FCC unit.

The gasoline obtained from the catalytic cracking unit has an end point that differs depending on whether a maxi gasoline or a maxi distillate mode is desired.

- for the maxi gasoline mode, the ex FCC gasoline is preferentially defined as C5-220° C.;
- for the maxi distillate mode, the ex FCC mode is preferentially defined as C5-150° C.

This distinction is important since, given the flexibility of the process, it is essential to keep in mind the definition of the FCC outlet gas which should be taken into account in each case.

The process of the invention may also function in accordance with a "maxi propylene" mode, which is compatible with any end point of the gasoline in the range 150° C. to 220° C. This "maxi propylene" mode is essentially obtained by the operating conditions of the catalytic cracking unit (known as "high severity" conditions) and by using a catalyst incorporating a certain proportion of ZSM-5 zeolite.

The pre-treated gasoline (SHU outlet) is then separated into two cuts by means of a distillation step termed a splitter (SPLIT):

- a cut termed light gasoline, which is rich in C5-C6, olefinic in nature and has a very low sulphur and diolefins content, with an end point in the range 50° C. to 150° C., preferentially in the range 50° C. to 100° C., and more preferably in the range 50° C. to 80° C.;
- a cut termed the heavy gasoline cut, having as its initial boiling point the end point of the light gasoline cut, and having an end point of 220° C. (in maxi gasoline or maxi propylene mode), or 150° C. (in maxi distillate mode) and which can be sent to a hydrodesulphurization unit in order to comply with commercial fuel specifications.

The light fraction (C5-Pf) of the hydrotreated gasoline cut, i.e. principally the C5-C6 fraction, or even in some cases C5-C7 or even C5-C9, to which it is optionally possible to add a certain proportion of C4 cut, is then sent to a purification section (PUR) upstream of the oligomerization unit (OLG) in order to reduce the nitrogen-containing compounds.

Depending on the catalyst employed and the operating conditions considered, the oligomerization unit (OLG) can be used to orientate production towards gasoline or middle distillate.

- in the maxi propylene operational mode, the whole of the effluent obtained from the oligomerization step constituted by a light gasoline cut, IP-150° C., heavy cut 150-220° C. and a "kero" cut with an initial point of more than 220° C. (abbreviated to 220° C.+) is recycled to the FCC;
- in the maxi gasoline operational mode, only the 220° C.+ "kero" portion of the oligomerizate is recycled to the FCC; the light and heavy gasolines are sent to the gasoline pool;
- in the maxi distillate operational mode, only the light gasoline cut, IP-150° C., will be recycled to the FCC. The middle distillate portion with an initial point of more than 150° C., denoted 150° C.+, requires a final hydrotreatment before being transformed into gas oil complying with commercial specifications.

The process of the present invention calls upon a step for selective hydrogenation (SHU) of the gasoline cut obtained from the catalytic cracking unit (FCC), which consists essentially of converting the diolefins into olefins and of making the sulphur-containing compounds heavier.

Thus, the light gasoline cut after the separation step (termed a splitter) has a reduced quantity of sulphur-containing compounds and dienes, namely the principal inhibitors of the oligomerization catalyst.

Adding the step for selective hydrogenation (SHU) of the ex FCC gasoline thus means that the cycle period for operating the oligomerization step (OLG) can be very significantly increased without altering the distribution of the desired products.

The gasoline selective hydrogenation unit (SHU) can be used for hydrogenation of the diolefins contained in the gasoline obtained from the catalytic cracking unit as well as for converting light sulphur-containing compounds into sulphur-containing compounds with a higher boiling point. Since the hydrogenation is selective, the olefins are hydrogenated to a lesser extent.

The gasoline which is hydrotreated thereby is then separated into two cuts at the splitter (SPLIT): a light gasoline, with a very low quantity of sulphur-containing compounds and which is rich in olefins, and a heavy gasoline cut which is then sent to a hydrodesulphurization unit.

The light gasoline is denoted C5-Pf.

The heavy gasoline is denoted Pf-150° C. or 220° C. (respectively in maxi distillate and in maxi gasoline mode).

Pf denotes the cut point separating the light gasoline cut and the heavy gasoline cut.

Pf is in the range 50° C. to 150° C., preferably in the range 50° C. to 100° C., and more preferably in the range 50° C. to 80° C.

The present invention is compatible with all catalytic cracking (FCC) reactor technologies, whether it be gas-solid upflow or gas-solid downflow technology.

The catalytic cracking unit (FCC) used in the present process can be differentiated into two modalities: with a single or with a plurality of reactors, each reactor possibly functioning in upflow or in downflow mode.

In the case of a plurality of oligomerization units (OLG) associated with a catalytic cracking unit (FCC), these latter may be arranged in series or in parallel.

More precisely, the present invention may be described as a process for converting a heavy hydrocarbon feed having great flexibility for the production of middle distillate, gasoline and propylene, carrying out the following steps:

a) a step for catalytic cracking (FCC) of the heavy cut, producing a C5-220° C. gasoline cut when the FCC is orientated towards the production of gasoline and C5-150° C. when the FCC is orientated towards the production of middle distillate;

b) a step for selective hydrogenation (SHU) of the gasoline cut obtained from the catalytic cracking unit (FCC), operating under the following conditions: a pressure in the range 0.5 to 5 MPa, a temperature in the range 80° C. to 220° C., with a liquid hourly space velocity (LHSV) in the range 1 $h^{-1}$ to 10 $h^{-1}$, the liquid hourly space velocity being expressed in liters of feed per liter of catalyst per hour (L/L·h);

c) a step for separating the gasoline obtained from step b) by distillation (SPLIT) in order to separate two cuts: a light C5-Pf gasoline cut and a heavy Pf-150° C. or Pf-220° C. gasoline cut depending on the end point of the gasoline leaving the FCC, the temperature Pf being the boundary between light gasoline and heavy gasoline and being in the range 50° C. to 150° C., preferably in the range 50° C. to 100° C., and more preferably in the range 50° C. to 80° C.;

d) a step for purification (PUR) of the Light C5-Pf gasoline obtained from step c) which is intended to reduce the nitrogen to less than 1 ppm by weight, preferably less than 0.2 ppm;

e) a step for oligomerization (OLG) of the light C5-Pf gasoline obtained from the purification step (PUR);

f) a step for separating the oligomers obtained from step e) in order to release at least two cuts:
- a C5-150° C. gasoline cut;
- a 150° C.+ distillate cut.

Optionally, a LPG raffinate may also be produced.

The remainder of the text provides information regarding the 3 modes of the process of the invention.

Maxi Propylene Operational Mode:

The maxi propylene mode is essentially obtained by employing the operating conditions of the FCC known as the high severity mode (reactor outlet temperature over 600° C.) and using a catalyst incorporating a certain proportion of ZSM-5 zeolite.

In the maxi propylene operational mode, the operating conditions for the oligomerization step (OLG) are as follows:
- temperature in the range 60° C. to 350° C., preferably in the range 100° C. to 300° C., and still more preferably in the range 120° C. to 250° C.;
- pressure in the range 1 to 10 MPa (1 MPa=$10^6$ Pascal), preferably in the range 2 to 8 MPa, and more preferably in the range 3 to 6 MPa;
- catalysts based on silica-alumina or amorphous aluminosilicate, or organic acid resin, or zeolites. Preferably, the catalysts are based on silica-alumina or on amorphous aluminosilicate or organic acid resin, still more preferably of the sulphonic resin type.

In this operational mode, the C5-150° C. gasoline cut and the 150° C.+ distillate cut obtained from the oligomer separation step are recycled to the FCC. Constituted principally by olefins, these recycles have a very high propylene potential under FCC cracking conditions.

Maxi Gasoline Operational Mode:

In the maxi gasoline operational mode, the operating conditions for the oligomerization step (OLG) are as follows:
- temperature in the range 60° C. to 350° C., preferably in the range 100° C. to 300° C., and still more preferably in the range 120° C. to 250° C.;
- pressure in the range 1 to 10 MPa (1 MPa=$10^6$ Pascal), preferably in the range 2 to 8 MPa, and more preferably in the range 3 to 6 MPa;
- catalysts based on silica-alumina or amorphous aluminosilicate, or organic acid resin, or crystalline zeolites. Preferably, the catalysts are based on silica-alumina or on amorphous aluminosilicate or organic acid resin, still more preferably of the sulphonic resin type.

In this operational mode, only the 150° C.-360° C. distillate cut obtained from the oligomer separation step may advantageously be recycled to the FCC, in order to improve the overall production of gasoline as well as the selectivity for gasoline over middle distillate.

Maxi Distillate Operational Mode:

In the maxi distillate operational mode, the operating conditions for the oligomerization step (OLG) are as follows:
- temperature in the range 100° C. to 400° C., preferably in the range 150° C. to 350° C.;
- pressure in the range 1 to 10 MPa, preferably in the range 2 to 8 MPa, and more preferably in the range 3 to 6 MPa;
- catalyst based on silica-alumina or amorphous aluminosilicate or crystalline zeolite preferably selected from the following zeolites: ferrierite, chabazite, Y and US-Y zeolites, ZSM-5, ZSM-12, NU-86, mordenite, ZSM-22, NU-10, ZBM-30, ZSM-11, ZSM-57, ZSM-35, IZM-2, ITQ-6 and IM-5, SAPO, used alone or as a mixture.

Highly preferably, said zeolite is selected from the group constituted by the ferrierite, ZSM-5, mordenite and ZSM-22 zeolites, used alone or as a mixture.

Still more preferably, the zeolite used is ZSM-5.

In this operational mode, only the light IP-150° C. gasoline cut can advantageously be recycled to the FCC. The middle distillate portion with a distillation range in the range 150° C. to 360° C. requires a final hydrotreatment in order to be transformed into gas oil complying with commercial specifications.

In another variation of the present invention, which is compatible with all of the variations described above, the steps of b) selective hydrogenation and c) separation into light gasoline and heavy gasoline are carried out in a single reactive distillation unit.

In the case in which the quantity of nitrogen of the light gasoline obtained from the separation step (SPLIT) is less than 1 ppm, and preferably less than 0.2 ppm, the purification step (PUR) located upstream of the oligomerization step (OLG) may be dispensed with.

DETAILED DESCRIPTION OF THE INVENTION

The invention concerns a process for converting a hydrocarbon feed termed a heavy feed, i.e. constituted by hydrocarbons with a boiling point of more than approximately 340° C.

The starting heavy hydrocarbon cut may be an atmospheric residue or a vacuum distillate.

The process of the invention comprises a catalytic cracking step (FCC), a unit for selective hydrogenation (SHU) of the gasoline produced from the catalytic cracking unit, a step for separation of the gasoline produced (SPLIT) into a light gasoline cut, with a low sulphur-containing compounds and diolefins content, and a heavy gasoline cut, and at least one step for oligomerization (OLG) of the light gasoline.

Optionally, oligomerization of the light gasoline cut may also be carried out as a mixture with all or a portion of the C3 and C4 cuts obtained from FCC or from other additional sources such as the coking unit, from visbreaking, from converting methanol into olefins or from any other process for converting alcohols into olefins, from steam cracking or even from a Fischer-Tropsch synthesis unit or from the dehydrogenation of paraffins, alone or as a mixture.

Selective hydrogenation (SHU) can be used to hydrogenate a portion of the diolefins to olefins, thereby substantially limiting the hydrogenation of olefins to paraffins.

In addition, it can be used to convert light sulphur-containing compounds into heavier sulphur-containing compounds.

Separation between the light C5 gasoline cut and the heavy gasoline with an end point of 150° C. or 220° C. (respectively in the maxi distillate or maxi gasoline mode) is carried out in one distillation (denoted SPLIT in FIG. 1).

In the present invention, the cut point Pf separating the light gasoline cut and the heavy gasoline cut is in the range 50° C. to 150° C., preferably in the range 50° C. to 100° C., and more preferably in the range 50° C. to 80° C.

The light gasoline cut, with a distillation range C5-Pf, which is sent to the oligomerization (OLG) contains:
- fewer than 10 carbon atoms, preferably fewer than 7 carbon atoms;
- less than 100 ppm (by weight) of sulphur, preferably less than 50 ppm, and more preferably less than 10 ppm (by weight);
- less than 2000 ppm (by weight) of diolefins, preferably less than 1000 ppm, and more preferably less than 500 ppm (by weight).

This light cut which is rich in olefins may then be sent to an oligomerization unit (OLG) in order to transform the olefins contained therein into heavier olefins which may be used as a gasoline or as middle distillates, as a function of the catalyst and the operating conditions employed in that step.

Separation in the splitter (SPLIT) between the light gasoline and the heavy gasoline can be used to:
- upgrade the olefins contained in the gasoline obtained from catalytic cracking, which are mainly C5-Pf olefins. This separation can be used to concentrate the reactive olefins with a view to subsequent oligomerization, in the light gasoline, and thus it can be sent directly to the oligomerization unit (OLG);
- The capacity of the oligomerization unit (OLG) can thus be reduced, which is beneficial in terms of investment and operating costs. In fact, the reactivity of olefins in oligomerization decreases greatly with the number of carbon atoms;
- of concentrating the sulphur-containing compounds in the heavy gasoline cut, since the SHU has made the sulphur-containing compounds heavier and which are then found in said heavy gasoline, typically sent to a selective hydrotreatment step.

The remainder of the description provides information regarding the various units constituting the concatenation of units of the present invention.

FCC Unit:

In general, the feed for the catalytic cracking unit is constituted by a vacuum distillate or possibly by an atmospheric residue. The overall cracked feed may contain up to 100% by weight of hydrocarbons with a boiling point of more than 340° C.

In certain cases corresponding to feeds for the FCC unit that are highly loaded with metals, sulphur-containing compounds and nitrogen-containing compounds, a pre-treatment may be carried out upstream of the FCC unit. This upstream FCC pre-treatment (not shown in FIG. 1) can on the one hand improve the activity of the SHU upstream of the oligomerization unit (OLG), and on the other hand displace the cut point between the light gasoline and the heavy gasoline at the splitter (SPLIT).

This displacement of the cut point to approximately 150° C. means that it is then possible to maximize the feed going to the oligomerization unit (OLG).

The gasolines obtained from the cracking units are generally rich in mono-olefins (between 20% and 50% by weight) and in sulphur (between 100 ppm and 2% by weight of sulphur), but also in diolefins in an amount which can vary between 1% by weight and 5% by weight.

Fractionation of the effluents from catalytic cracking (FCC) can be used to obtain several cuts:
- a C3 cut which is rich in compounds containing 3 carbon atoms, in particular propylene;
- a C4 cut which is rich in compounds containing 4 carbon atoms, in particular butenes;
- a gasoline cut containing olefins containing 5 or more carbon atoms, with an end point of 220° C. when a maxi gasoline mode is sought, and 150° C. when a maxi distillate mode is sought.

This gasoline cut will be abbreviated to C5-220° C. (maxi gasoline mode) or C5-150° C. (maxi distillate mode).

The catalytic cracking unit (FCC) comprises a reactor which may be in upflow or downflow mode.

When catalytic cracking is carried out in a single upflow reactor, the reactor outlet temperature (ROT) is in the range 450° C. to 650° C., preferably in the range 470° C. to 620° C., and the C/O ratio is in the range 2 to 20, preferably in the range 4 to 15.

When the reactor is in downflow mode, the reactor outlet temperature (ROT) is in the range 480° C. to 650° C., and the C/O ratio is in the range 10 to 50.

In accordance with the invention, the catalytic cracking catalyst is constituted by a matrix of alumina, silica or silica-alumina with or without an ultra-stable Y type zeolite dispersed in that matrix.

Adding an additive based on ZSM-5 zeolite, the quantity of ZSM-5 crystals in the total inventory for the catalytic cracking unit (FCC) being less than 30% by weight, may also be envisaged.

The catalyst for the FCC reactor is typically constituted by particles with a mean diameter that is generally in the range 40 to 140 micrometers, usually in the range 50 to 120 micrometers.

The catalyst may also comprise at least one zeolite with form selectivity with one of the following structure types: MEL (for example ZSM-11), MFI (for example ZSM-5), NES, EUO, PER, CHA (for example SAPO-34), MFS, MWW.

It may also comprise one of the following zeolites: NU-85, NU-86, NU-88 and IM-5, which also have form selectivity.

The advantage of these zeolites with form selectivity is that better propylene/isobutene selectivity is obtained, i.e. a higher propylene/isobutene ratio in the effluents from the catalytic cracking unit (FCC).

The proportion of zeolite with form selectivity with respect to the total quantity of zeolite may vary as a function of the feeds used and of the structure of the desired products. Frequently, 0.1% to 60%, preferably 0.1% to 40%, and in particular 0.1% to 30% by weight of zeolite with form selectivity will be used.

The zeolite or zeolites may be dispersed in a matrix based on silica, alumina or silica-alumina, the proportion of zeolite (all zeolites together) with respect to the weight of catalyst is frequently in the range 0.7% to 80% by weight, preferably in the range 1% to 50% by weight, and still more preferably in the range 5% to 40% by weight.

In the case in which a plurality of zeolites are used, they may be incorporated into a single matrix or into several different matrices. The quantity of zeolite with form selectivity in the total amount is less than 30% by weight.

The catalyst used in the catalytic cracking reactor (FCC) may be constituted by an ultra-stable Y type zeolite dispersed in a matrix of alumina, silica, or silica-alumina, to which an additive based on ZSM-5 zeolite is added, the quantity of ZSM-5 crystals in the total inventory being less than 30% by weight.

Selective Hydrogenation Unit (SHU):

The gasoline cut, which is rich in olefins but contains diolefins and sulphur-containing compounds, is then sent to a selective hydrogenation unit (SHU). On this unit, the diolefins are hydrogenated in the presence of hydrogen into olefins without major hydrogenation of the olefins, and the light sulphur-containing compounds are converted into sulphur-containing compounds with a higher boiling point.

Patent FR 2 935 389 A1 describes a catalytic system used in the process for the selective hydrogenation of gasoline.

The catalyst used on the selective hydrogenation step may also be that described in patent FR 2 935 389 B1. It contains at least one metal from group VIB and at least one non-noble metal from group VIII deposited on a porous support, and in which:

the quantity by weight of oxide of the element from group VIB is in the range 4% to 20% by weight;

the quantity by weight of oxide of the element from group VIII is less than 15% by weight.

Selective hydrogenation (SHU) consists of passing a mixture constituted by the gasoline to be treated and hydrogen over one of the catalysts defined above.

The hydrogen is generally introduced in a slight excess, up to 5 mole per mole, with respect to the stoichiometric quantity, necessary for hydrogenation of the diolefins (one mole of hydrogen per mole of diolefin).

The mixture constituted by the gasoline and hydrogen is brought into contact with the catalyst at a pressure in the range 0.5 to 5 MPa, a temperature in the range 80° C. to 220° C., with a liquid hourly space velocity (HSV) in the range 1 $h^{-1}$ to 10 $h^{-1}$, the liquid hourly space velocity being expressed in liters of feed per liter of catalyst per hour (L/L·h).

Separation Unit (SPLIT)

This selective hydrogenated gasoline cut is then sent to a separation column (denoted SPLIT) in order to separate the gasoline into two cuts: a cut termed the light gasoline and a cut termed the heavy gasoline cut.

The light gasoline cut, C5-Pf, contains:
  fewer than 10 carbon atoms, preferably fewer than 7 carbon atoms;
  less than 100 ppm by weight of sulphur, preferably less than 50 ppm, more preferably less than 10 ppm (by weight);
  less than 2000 ppm (by weight) of diolefins, preferably less than 1000 ppm, and more preferably less than 500 ppm (by weight). The light gasoline cut is sent to an oligomerization unit (OLG).

The heavy gasoline cut is a Pf-220° C. cut in which the sulphur-containing compounds have been concentrated. This heavy gasoline cut is then sent to a hydrodesulphurization unit before being sent to the gasoline pool.

The C3 and C4 cuts produced from the catalytic cracking unit (FCC) may also be sent, in part or as a whole, to the oligomerization unit (OLG), depending on the requirements of the refinery.

Preferably, the propylene contained in the C3 cut is upgraded as a product, while the C4 cut is sent, as a mixture with the C5-C6 light gas, to the pre-treatment of the oligomerization unit (OLG).

Separation between the light gasoline and the heavy gasoline after the selective hydrogenation step is preferably carried out using a conventional distillation column also known as a "splitter".

This column generally operates at a pressure in the range 0.1 to 2 MPa, preferably in the range 0.2 to 1 MPa. The number of theoretical plates in this separation column is generally in the range 10 to 100, preferably in the range 20 to 60.

The reflux ratio, expressed as being the external reflux in kg/h divided by the flow rate supplying the column expressed in kg/h, is generally less than unity, preferably less than 0.7.

The quantity of sulphur in the light gasoline obtained from the separation unit (SPLIT) which is then sent to the oligomerization (OLG) is less than 100 ppm, preferably less than 50 ppm and more preferably less than 10 ppm.

Purification Unit (PUR)

The concatenation of selective hydrogenation (SHU) and separation of a light gasoline cut (SPLIT) can be used to prepare an oligomerization feed with a reduced quantity of diolefins and sulphur-containing compounds, which are inhibitors. It cannot generally be used to reduce the quantity of nitrogen-containing compounds, which are poisons for the oligomerization catalysts. It is thus necessary to insert a specific purification step in order to reduce the total quantity of nitrogen to less than 1 ppm by weight.

This purification step (PUR) uses any technique known to the skilled person, and in particular may employ:
  adsorbents such as aluminas, silica-aluminas or molecular sieves, these latter preferably being based on zeolites of the NaX or NaY type;
  prior washing with water followed by adsorption onto the adsorbents cited above, preferably onto molecular sieves.

Oligomerization Unit (OLG)

Oligomerization is distinguished from polymerization by having a limited number of added molecules. In the context of the invention, the number of molecules adding together is in the range 2 to 10, limits included, and generally in the range 2 to 5.

The oligomerizates may, however, include traces of olefins that have been oligomerized with a number of molecules of more than 10. Usually, these traces represent less than 5% by weight with respect to the oligomers formed.

Oligomerization may be carried out in one or more steps, with one or more reactors arranged in parallel or in series, and one or more catalysts. The following description of the catalyst and the operating conditions may be applied to any one of the steps and/or to any one of the reactors.

The oligomerization catalyst used is preferably a catalyst based on silica-alumina, aluminosilicate or zeolitic alumina, or organic acid resin, preferably of the sulphonic resin type.

In maxi gasoline operational mode for the oligomerization, the preferred catalysts are catalysts based on silica-alumina or amorphous aluminosilicate, or organic acid resin, preferably of the sulphonic acid type, and the operating conditions are as follows:
  temperature in the range 60° C. to 300° C., preferably in the range 80° C. to 250° C.;
  pressure in the range 1 to 10 MPa (1 MPa=$10^6$ Pascal), preferably in the range 2 to 8 MPa and more preferably in the range 3 to 6 MPa.

In the maxi distillate operational mode for oligomerization, the preferred catalysts are catalysts based on silica-alumina or amorphous aluminosilicate, or crystalline zeolites preferably selected from the following zeolites: ferrierite, chabazite, Y and US-Y zeolites, ZSM-5, ZSM-12, NU-86, mordenite, ZSM-22, NU-10, ZBM-30, ZSM-11, ZSM-57, ZSM-35, IZM-2, ITQ-6 and IM-5, SAPO, used alone or as a mixture.

Highly preferably, said zeolite is selected from the group constituted by the ferrierite, ZSM-5, mordenite and ZSM-22 zeolites, used alone or as a mixture.

Still more preferably, the zeolite used is ZSM-5.

The operating conditions for oligomerization (OLG) in the maxi distillate operational mode are as follows:
  temperature in the range 100° C. to 400° C., preferably in the range 150° C. to 350° C.;
  pressure in the range 1 to 10 MPa, preferably in the range 2 to 8 MPa, more preferably in the range 3 to 6 MPa.

The oligomerizates obtained from the oligomerization unit (OLG) are then separated by distillation into at least two cuts, a gasoline cut and a middle distillates cut.

The gasoline cut has a boiling point of less than 220° C., preferably less than 150° C.

The middle distillate cut has an initial boiling point of more than 130° C., preferably more than 150° C.

Optionally, a portion of the gasoline produced at the end of the oligomerization step may be recycled to the oligomerization reactor so as to increase the production of middle distillates.

The olefins are oligomerized to obtain a mixture of hydrocarbons containing mono olefins containing mainly 8 or more carbon atoms. Typically, from C4 olefins, oligomers are obtained which primarily contain 30 or fewer carbon atoms, and mainly in the range 8 to 20.

Figure 1:
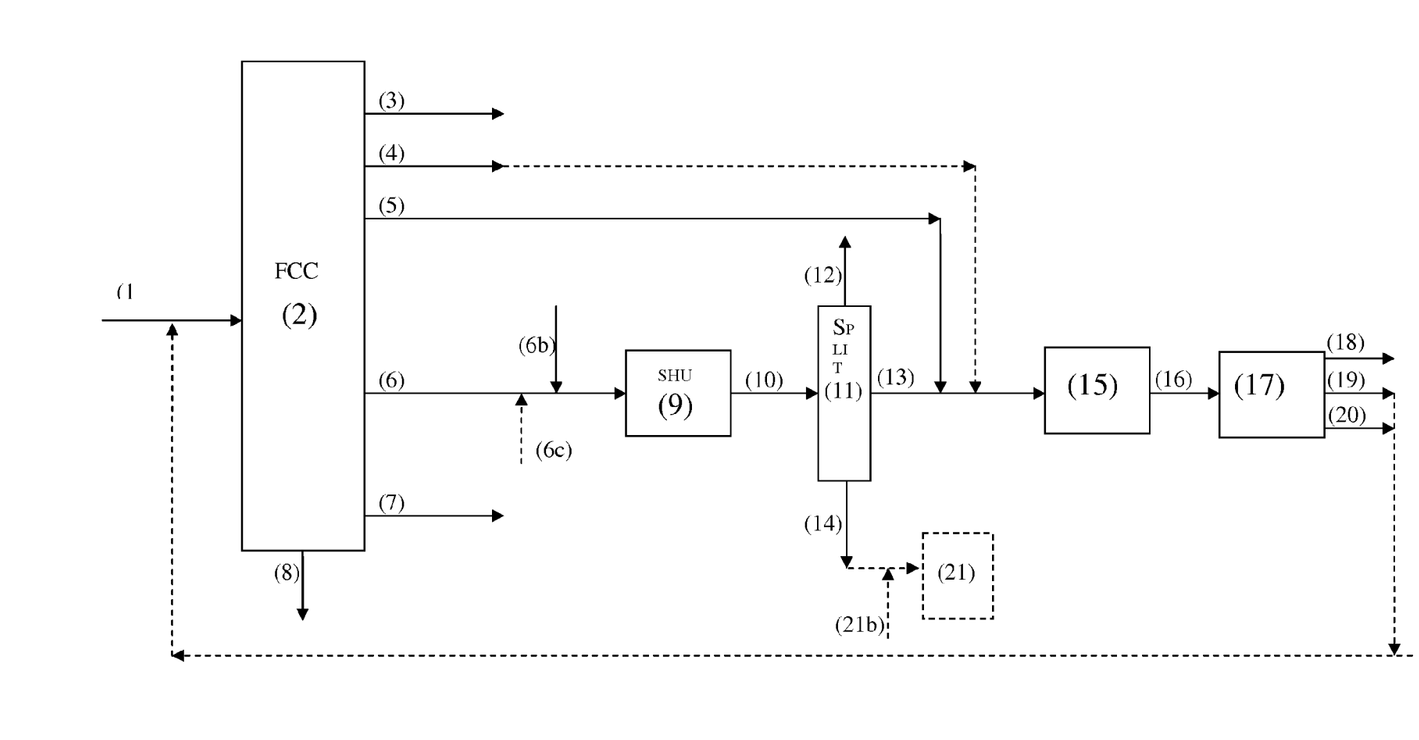

FIG. 1 represents the layout of the process of the present invention.

The feed 1 is introduced into the catalytic cracking unit FCC, 2, from which the following are extracted, in increasing molecular weight order:
- a dry gas cut 3 constituted by hydrogen ($H_2$), methane and possibly ethane, ethylene and propane;
- a C3 cut 4 formed by molecules of hydrocarbon containing 3 carbon atoms, rich in propylene;
- a C4 cut 5 formed by molecules of hydrocarbons containing 4 carbon atoms, rich in butenes;
- a gasoline cut 6 with a distillation range in the range 25° C. to 220° C.;
- a "middle distillates" cut 7 with a distillation range in the range 220° C. to 360° C.;
- a cut 8 termed a "slurry" which joins the fuel pool.

The gasoline cut 6, mixed with a hydrogen makeup 6b and/or a secondary source of olefins 6c, is sent to the gasoline selective hydrogenation unit 9 from which the effluent 10 is separated, in a distillation column 11, into a plurality of cuts:
- a purge 12 composed of light gases (hydrogen, cracking gas such as methane, ethane);
- a light gasoline cut 13 composed of C5 hydrocarbons up to an end point boiling at Pf° C.;
- a heavy gasoline cut 14 composed of hydrocarbons with a distillation range in the range Pf° C. to 220° C.

The value of the temperature Pf, being the cut point between the light gasoline and the heavy gasoline, is in the range 50° C. to 150° C., preferably in the range 50° C. to 100° C., and more preferably in the range 50° C. to 80° C.

The light gasoline cut 13 is then sent as a mixture with the C4 cut 5 to a series of purification units 15 which produces the feed 16 for the oligomerization unit.

Optionally, the C3 cut 4 may be mixed with the light gasoline cut to be oligomerized.

At least two cuts are extracted from this oligomerization unit 17:
- a cut 18 termed the raffinate, which corresponds to unconverted olefins and to paraffins of the C3, 4, and C4, 5, feeds;
- a gasoline cut 19, which corresponds to the paraffins contained in the cut 13 as well as to a portion of the oligomerizates formed originating from the cuts 5 and 4 and 13;
- a middle distillates cut 20 corresponding to the heavy oligomerizates formed from cuts 4, 5, 13, with a distillation range of 150° C.-360° C. which is sent for hydrotreatment with a view to producing a gas oil to commercial specifications.

The heavy gasoline cut 14 may optionally be sent as a makeup with hydrogen 21b to a gasoline hydrodesulphurization unit 21.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding application No. FR 12/00.424, filed Feb. 15, 2012 are incorporated by reference herein.

EXAMPLES

The examples below were designed to illustrate the various modes of operation of the process of the present invention, more particularly at the level of the oligomerization unit (OLG), and to demonstrate the importance of using a selective hydrogenation (SHU) upstream of said oligomerization unit.

The examples are combined as follows:
Example A (with SHU)/Example B (without SHU).
Example C (with SHU)/Example D (without SHU);
Example E (with SHU).

Example A

In Accordance with the Invention

In this example, the light gasoline oligomerization unit (OLG) used an organic acid resin type catalyst (sulphonic resin).

The layout was as follows: selective hydrogenation (SHU), splitter (SPLIT), oligomerization (OLG) carried out on the C5/C6 recovered overhead from the splitter and fractionation to separate the residual 150° C. gasoline from the 150° C.+ fraction sent to an existing conventional kerosene hydrotreatment.

The selective hydrogenation (SHU) was carried out at 160° C., at a pressure of 2.0 MPa, at an hourly space velocity of 3 $h^{-1}$.

The $H_2$/feed ratio, expressed in liters of hydrogen per liter of feed, was 5 L/L and the catalyst was the HR845 catalyst sold by Axens.

The light gasoline oligomerization unit (OLG) used an organic acid resin type catalyst (sulphonic resin).

It was a catalyst sold by Axens with the name TA801. It was used under the following conditions: fixed bed reactor containing 50 tonnes of catalyst, pressure fixed at 3 MPa, temperature increasing between 60° C. and 160° C. in order to maintain a constant production of oligomers between the start and end of the cycle. The cycle period was 2 months.

The properties of the feed and products are given in Table 1 below:

TABLE 1

|  | Total gasoline from FCC | Overhead splitter ex SHU PG+ | Gasoline produced ex olig 150− | Kerosene after HDT, 150+ |
|---|---|---|---|---|
| Density | 0.74 | 0.66 | 0.668 | 0.778 |
| Total sulphur content, ppm | 600 | 50 | <10 | <1 |
| Nitrogen content, ppm | 50 | 7 | | |
| Diolefins content % by wt | 1.2 | 0.1 | — | |
| Olefins content, % by wt | 48 | 64 | 48.5 | <1 |
| RVP, kPa | 58 | 110 | 90. | |
| RON | 92 | 96.3 | 94.4 | |
| Smoke point, mm | | — | | 40 |
| Crystal disappearance point | | — | | <−65° C. |
| Flash point | | — | | 45.5 |
| Cloud point | | — | | <−48° C. |

The material balance, based on the light gasoline described above, is given in Table 2 below. This example clearly shows the important of selective hydrogenation (SHU) on the performance.

TABLE 2

| Feed, t/h | |
|---|---|
| Total FCC gasoline | 80 |
| Light gasoline to oligomerization | 25 |
| Products, t/h | |
| Gasoline produced, 150-° C. | 17 |
| Kerosene produced | 8 |

Example B

In Accordance with the Prior Art

This example, in accordance with the prior art, is intended to show the importance of introducing the selective hydrogenation unit (SHU) to the ex FCC gasoline. It should be compared with Example A above.

The layout was as follows: splitter (SPLIT), oligomerization (OLG) carried out on the C5/C6 recovered overhead from the splitter, and fractionation to separate the residual 150° C. gasoline from the heavy 150° C.+ fraction sent to an existing conventional kerosene hydrotreatment.

Selective hydrogenation was not present, unlike the case with Example A.

The properties of the feeds are given in Table 3 below.

It will be noted that the feed for the oligomerization unit (OLG) was much richer in sulphur and dienes than in case A.

TABLE 3

| | Total gasoline from FCC | Overhead splitter, no SHU |
|---|---|---|
| Density | 0.74 | 0.66 |
| Total sulphur content, ppm | 600 | 210 |
| Nitrogen content, ppm | 50 | 7 |
| Diolefins content % by wt | 1.2 | 1.0 |
| Olefins content, % by wt | 48 | 64 |
| RVP, kPa | 58 | 110 |
| RON | 92 | 96.3 |
| Smoke point, mm | | |
| Crystal disappearance point | | |
| Flash point | | |
| Cloud point | | |

The oligomerization catalyst TA801 was used under the same conditions as in Example A. This time, the temperature at the start of the cycle was 100° C., and the cycle period was less than 1 month.

The distribution and quality of the products were the same as in Example A, in accordance with the invention.

Example C

In Accordance with the Invention

In this example, the light gasoline oligomerization unit (OLG) used a catalyst based on amorphous aluminosilicate.

The layout was as follows: selective hydrogenation (SHU)/splitter (SPLIT) and elimination of nitrogen-containing compounds on 13x molecular sieve carried out on the C5/C6 recovered overhead from the splitter, then oligomerization (OLG) on silica-alumina and fractionation to separate the residual 150° C. gasoline from the heavy 150° C.+ fraction sent to an existing hydrotreatment unit.

The selective hydrogenation was carried out under the same conditions as in Example A.

The splitter was regulated to obtain the overhead cut indicated in the table below, with a reduced quantity of impurities. The nitrogen-containing compounds were captured by using a fixed bed operating at 30° C. and containing a molecular sieve (NaX zeolite) until a residual nitrogen content of less than 1 ppm was obtained.

The light gasoline oligomerization unit used a catalyst constituted by silica-alumina. It was a commercial catalyst sold by Axens with the name IP811.

It was used under the following conditions: fixed bed reactor containing 50 tonnes of catalyst, pressure fixed at 6 MPa, temperature increasing between 120° C. and 250° C. between the start and end of the cycle, to keep the oligomer production constant.

The cycle period was 3 months.

The properties of the feeds and products are given in Table 4 below.

TABLE 4

| | Total gasoline from FCC | Overhead splitter ex SHU PG+ | Gasoline produced, ex oligo | Kerosene after HDT |
|---|---|---|---|---|
| Density | 0.74 | 0.655 | 0.66 | 0.783 |
| Total sulphur content, ppm S | 600 | 15 | 10 | <1 |
| Nitrogen content, ppm N | 50 | 5 | | |
| Diolefins content % by wt | 1.2 | 0.05 | | |
| Olefins content, % by wt | 48 | 65 | 29 | <1 |
| RVP, kPa | 58 | 115 | 110 | |
| RON | 92 | 96.5 | 92.5 | |
| Smoke point, mm | | | | 35 |
| Crystal disappearance point | | | | <−70° C. |
| Flash point | | | | 43.5 |
| Cloud point | | | | <−58° C. |

The material balance based on the light gasoline is given in Table 5 below.

This example clearly shows the importance of the selective hydrogenation (SHU) on performance.

TABLE 5

| Feed, t/h | |
|---|---|
| Total FCC gasoline | 86 |
| Light gasoline | 25 |
| Products, t/h | |
| Gasoline produced, 150-° C. | 14 |
| Kerosene produced | 11 |

Example D

In Accordance with the Prior Art

In this case, the layout was as follows: splitter (SPLIT) and oligomerization carried out on the C5/C6 recovered overhead from the splitter and fractionation to separate the residual 150° C. gasoline from the heavy 150° C.+ fraction sent to an existing hydrotreatment unit.

Selective hydrogenation did not exist, unlike in Example C.

The properties of the feeds are given in Table 6 below.

It will be noted that the feed for the oligomerization unit was much richer in sulphur and in dienes than in case C.

The oligomerization catalyst IP811 was used under the same conditions as for Example C.

The temperature at the start of the cycle this time was 210° C., and the cycle period was 20 days.

The distribution and quality of the products were the same as in Example C in accordance with the invention.

TABLE 6

|  | Total gasoline from FCC | Overhead splitter no SHU |
|---|---|---|
| Density | 0.74 | 0.655 |
| Total sulphur content, ppm | 1200 | 180 |
| Nitrogen content, ppm | 50 | 5 |
| Diolefins content, % by wt | 1.5 | 1.0 |
| Olefins content, % by wt | 48 | 65 |
| RVP, kPa | 58 | 115 |
| RON | 92 | 96.5 |

Example E

In Accordance with the Invention

In this example, the light gasoline oligomerization unit (OLG) used a catalyst based on zeolite.

The layout was as follows: selective hydrogenation (SHU), splitter (SPLIT) and elimination of nitrogen-containing compounds on 13x molecular sieve, carried out on the C5/C6 recovered overhead from the splitter, then oligomerization (OLG) over zeolite and fractionation to separate the residual 150° C. gasoline from the heavy 150° C.+ fraction sent to an existing hydrotreatment unit, HDT, to produce a high quality diesel.

The selective hydrogenation (SHU) was carried out under the same conditions as in Example A.

The splitter was regulated to obtain the overhead cut indicated in the table below, with a reduced impurities content, as in Example C.

The nitrogen-containing compounds were captured by using a fixed bed containing molecular sieve (NaX zeolite), until the residual nitrogen content was less than 1 ppm.

The light gasoline oligomerization unit used a catalyst based on commercial ZSM-5 zeolite.

It was used under the following conditions: fixed bed reactor containing 40 tonnes of catalyst, pressure fixed at 6 MPa, temperature increasing between 200° C. and 330° C. between the start and end of the cycle, to keep the oligomer production constant.

The cycle period was 60 days.

The properties of the feeds and products are given in Table 7 below:

TABLE 7

|  | Total gasoline from FCC | Overhead splitter ex SHU PG+ | Gasoline produced 150− | Diesel after HDT 150 + |
|---|---|---|---|---|
| Density | 0.74 | 0.655 | 0.695 | 0.797 |
| Total sulphur content, ppm | 1200 | 15 | 10 | <1 |
| Nitrogen content, ppm | 50 | 5 |  | <1 |
| Diolefins content, % by wt | 1.5 | 0.05 |  |  |
| Olefins content, % by wt | 48 | 65 | 26 | <1 |
| RVP, kPa | 58 | 115 | 105 |  |

TABLE 7-continued

|  | Total gasoline from FCC | Overhead splitter ex SHU PG+ | Gasoline produced 150− | Diesel after HDT 150 + |
|---|---|---|---|---|
| RON | 92 | 96.5 | 90 |  |
| Crystal disappearance point |  |  |  | <−50° C. |
| Flash point |  |  |  | 65 |
| Cloud point |  |  |  | <−48° C. |
| Motor cetane number |  |  |  | 50 |

The material balance is given in Table 8 below:

TABLE 8

| Feed, t/h |  |
|---|---|
| Total FCC gasoline | 86 |
| Light gasoline | 25 |
| Products, t/h |  |
| Gasoline produced, 160-° C. | 13 |
| Diesel produced | 12 |

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A process for converting a heavy hydrocarbon feed having great flexibility for the production of propylene, gasoline and middle distillate, carrying out the following steps when the process operates in maxi propylene mode:
   a) catalytic cracking (FCC) of the heavy cut, producing a C5-220° C. gasoline cut when the FCC is orientated towards the production of gasoline and C5-150° C. when the FCC is orientated towards the production of middle distillate;
   b) selective hydrogenation (SHU) of the gasoline cut obtained from the catalytic cracking unit (FCC), operating under the following conditions: a pressure in the range 0.5 to 5 MPa, a temperature in the range 80° C. to 220° C., with a liquid hourly space velocity (LHSV) in the range 1 $h^{-1}$ to 10 $h^{-1}$, the liquid hourly space velocity being expressed in liters liters of feed per liter of catalyst per hour (L/L·h);
   c) separating the gasoline obtained from step b) by distillation (SPLIT) in order to separate two cuts: a light C5-Pf gasoline cut and a heavy Pf-220° C. gasoline cut, the temperature Pf, being the boundary between light gasoline and heavy gasoline, being in the range 50° C. to 150° C.;
   d) purification (PUR) of the light C5-Pf gasoline obtained from step c) which reduces the nitrogen to less than 1 ppm by weight;
   e) oligomerization (OLG) of the light C5-Pf gasoline obtained from the purification step (PUR), the operating conditions for said oligomerization step (OLG) being as follows:
   temperature in the range 60° C. to 350° C.;
   pressure in the range 1 to 10 MPa (1 MPa=$10^6$ Pascal);
   catalysts based on silica-alumina or amorphous aluminosilicate, or organic acid resin, or zeolites;

f) separating the oligomers obtained from step e) in order to release at least two cuts:
- a C5-150° C. gasoline cut;
- a 150° C.+ distillate cut;

the process operating in maxi propylene mode wherein the C5-150° C. gasoline cut and the 150° C.+ distillate cut obtained from the oligomer separation step are recycled to the FCC.

2. A process for converting a heavy hydrocarbon feed having great flexibility for the production of middle distillate, gasoline and propylene, carrying out the following steps when the process operates in maxi gasoline mode:
   a) catalytic cracking (FCC) of the heavy cut, producing a C5-220° C. gasoline cut when the FCC is orientated towards the production of gasoline and C5-150° C. when the FCC is orientated towards the production of middle distillate;
   b) selective hydrogenation (SHU) of the gasoline cut obtained from the catalytic cracking unit (FCC), operating under the following conditions: a pressure in the range 0.5 to 5 MPa, a temperature in the range 80° C. to 220° C., with a liquid hourly space velocity (LHSV) in the range 1 $h^{-1}$ to 10 $h^{-1}$, the liquid hourly space velocity being expressed in liters of feed per liters of catalyst per hour (L/L·h);
   c) separating the gasoline obtained from step b) by distillation (SPLIT) in order to separate two cuts: a light C5-Pf gasoline cut and a heavy Pf-150° C. or Pf-220° C. gasoline cut, the temperature Pf, being the boundary between light gasoline and heavy gasoline, being in the range 50° C. to 150° C.;
   d) purification (PUR) of the light C5-Pf gasoline obtained from step c) which is intended to reduce the nitrogen to less than 1 ppm by weight;
   e) oligomerization (OLG) of the light C5-Pf gasoline obtained from the purification step (PUR), operating under the following conditions:
      temperature in the range 60° C. to 350° C.;
      pressure in the range 1 to 10 MPa (1 MPa=$10^6$ Pascal);
      catalysts based on silica-alumina or amorphous aluminosilicate, or organic acid resin, or crystalline zeolites;
   f) separating oligomers obtained from step e) in order to release at least two cuts:
      a C5-150° C. gasoline cut;
      a 150° C.+ distillate cut;
   the process operating in maxi gasoline mode wherein the 150° C.+ distillate cut obtained from the oligomer separation step after the oligomerization step (OLG) is recycled to the FCC.

3. A process for converting a heavy hydrocarbon feed having great flexibility for the production of middle distillate, gasoline and propylene, carrying out the following steps when the process operates in maxi distillate mode:
   a) catalytic cracking (FCC) of the heavy cut, producing a C5-220° C. gasoline cut when the FCC is orientated towards the production of gasoline and C5-150° C. when the FCC is orientated towards the production of middle distillate;
   b) selective hydrogenation (SHU) of the gasoline cut obtained from the catalytic cracking unit (FCC), operating under the following conditions: a pressure in the range 0.5 to 5 MPa, a temperature in the range 80° C. to 220° C., with a liquid hourly space velocity (LHSV) in the range 1 $h^{-1}$ to 10 $h^{-1}$, the liquid hourly space velocity being expressed in liters of feed per liters of catalyst per hour (L/L·h);
   c) separating the gasoline obtained from step b) by distillation (SPLIT) in order to separate two cuts: a light C5-Pf gasoline cut and a heavy Pf-150° C. or Pf-220° C. gasoline cut, the temperature Pf, being the boundary between light gasoline and heavy gasoline, being in the range 50° C. to 150° C.;
   d) purification (PUR) of the light C5-Pf gasoline obtained from step c) which is intended to reduce the nitrogen to less than 1 ppm by weight;
   e) a step for oligomerization (OLG) of the light C5-Pf gasoline obtained from the purification step (PUR), the operating conditions for said oligomerization step (OLG) being as follows:
      temperature in the range 100° C. to 400° C.;
      pressure in the range 1 to 10 MPa;
      catalyst based on silica-alumina or amorphous aluminosilicate or crystalline zeolite, used alone or as a mixture;
   f) separating oligomers obtained from step e) in order to release at least two cuts:
      a C5-150° C. gasoline cut;
      a 150° C.+ distillate cut;
   the process operation in maxi distillate mode wherein the C5-150° C. gasoline cut is recycled to the FCC.

4. The process for converting a heavy hydrocarbon feed having a high flexibility for the production of middle distillate, gasoline and propylene according to claim 3, in which the catalyst for the oligomerization unit is ferrierite, ZSM-5, mordenite or ZSM-22 zeolite, used alone or as a mixture.

5. The process for converting a heavy hydrocarbon feed having a high flexibility for the production of middle distillate, gasoline and propylene according to claim 1, in which the purification unit (PUR) located upstream of the oligomerization unit (OLG) uses a prior wash with water followed by adsorption onto an adsorbent.

6. The process according to claim 1, wherein step c) is at a temperature of 50 to 80° C.

7. The process according to claim 1, wherein step d) reduces the nitrogen to less than 0.2 ppm.

8. The process according to claim 1, wherein step e) is conducted at 120°-250° C. and 306 MPa, with a sulfonic resin catalyst.

9. The process according to claim 2, wherein step c) is at a temperature of 50° to 80° C.

10. The process according to claim 2, wherein step d) reduces the nitrogen to less than 0.2 ppm.

11. The process according to claim 2, wherein step e) is conducted at 120°-250° C. and 306 MPa, with a sulfonic resin catalyst.

12. The process according to claim 3, wherein c) is at a temperature of 50 to 80° C., step d) reduces nitrogen to less than 0.2 ppm and e) is conducted at 150° to 350° C., 3-6 MPa and with a ferrierite, chabazite, Y or US-Y zeolite, ZSM-5, ZSM-12, NU-86, mordenite, ZSM-22, NU-10, ZBM-30, ZSM-11, ZSM-57, ZSM-35, IZM-2, ITQ-6, IM-5, or SAPO catalyst.

13. The process according to claim 4, wherein the catalyst for the oligomerization unit is ZSM-5.

14. The process according to claim 5, wherein the adsorbent is an alumina, silica-alumina, or a molecular sieve.

15. The process according to claim 5, wherein the adsorbent is an NaX or NaY zeolite.

* * * * *